United States Patent [19]

Martin et al.

[11] 4,242,278
[45] Dec. 30, 1980

[54] PROCESS FOR THE PREPARATION OF 2-(2',2',2'-TRIHALOGENOETHYL)-4-HALOGENOCYCLOBUTAN-1-ONES

[75] Inventors: Pierre Martin, Rheinfelden; Hans Greuter, Eiken; Eginhard Steiner, Füllinsdorf; Daniel Bellus, Riehen, all of Switzerland

[73] Assignee: Ciba-Geigy Corporation, Ardsley, N.Y.

[21] Appl. No.: 948,126

[22] Filed: Oct. 3, 1978

Related U.S. Application Data

[63] Continuation-in-part of Ser. No. 891,412, Mar. 29, 1978, abandoned.

[30] Foreign Application Priority Data

Mar. 31, 1977 [CH] Switzerland ............... 4071/77
Nov. 24, 1977 [CH] Switzerland ............. 14404/77
Feb. 23, 1978 [CH] Switzerland ............... 1974/78
Sep. 25, 1978 [CH] Switzerland ............... 9992/78

[51] Int. Cl.³ ............... C07C 45/45; C07C 49/105; C07C 49/115
[52] U.S. Cl. ............... 568/341; 568/364; 568/367; 560/118; 560/124; 562/500; 562/506; 568/381
[58] Field of Search ............ 260/586 R, 586 C, 586 G

[56] References Cited

U.S. PATENT DOCUMENTS

| | | | |
|---|---|---|---|
| 3,642,904 | 2/1972 | Langkammerer | 260/590 |
| 3,655,765 | 4/1972 | Gelfand | 260/586 R |
| 4,028,418 | 6/1977 | van den Brink et al. | 260/586 C |
| 4,064,174 | 12/1977 | Verbrugge | 260/586 C |

FOREIGN PATENT DOCUMENTS 2654060 3/1978 Fed. Rep. of Germany .

1194604 6/1970 United Kingdom .

OTHER PUBLICATIONS

J. Am. Chem. Soc., 87, 5257, (1965).
Tetrahedron Letters, No. 1, 135–139, (1966).

*Primary Examiner*—Natalie Trousof
*Assistant Examiner*—Vera C. Clarke
*Attorney, Agent, or Firm*—Harry Falber

[57] ABSTRACT

A process for the preparation of 2-(2',2',2',-trihalogenoethyl)-4-halogenocyclobutan-1-ones of the formula

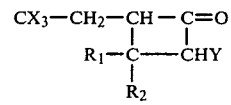

in which one of the radicals $R_1$ and $R_2$ is methyl and the other is hydrogen or methyl, or $R_1$ and $R_2$ together are an alkylene group having 2 to 4 carbon atoms, and X and Y are each chlorine or bromine, comprising reacting a 2,4,4,4-tetrahalogenobutyric acid chloride in the presence of an organic base with an ethylene compound which is disubstituted in 1-position by the radicals $R_1$ and $R_2$, as defined above, to form a 2-(2',2',2'-trihalogenoethyl)-2-halogenocyclobutan-1-one and then rearranging the latter, in the presence of a catalyst, into a 2-(2',2',2'-trihalogenoethyl)-4-halogenocyclobutan-1-one of the above formula; said 2-(2',2',2'-trihalogenoethyl)-4-halogenocyclobutan-1-ones being valuable intermediates for the preparation of 2-(2',2'-dihalogenovinyl)-cyclopropanecarboxylic acid and its insecticidally active esters; as well as the 2-(2',2',2'-trihalogenoethyl)-4-halogenocyclobutan-1-ones of the above formula and the intermediates utilized for their preparation.

21 Claims, No Drawings

PROCESS FOR THE PREPARATION OF 2-(2',2',2'-TRIHALOGENOETHYL)-4-HALOGENOCYCLOBUTAN-1-ONES

RELATED APPLICATIONS

This is a continuation-in-part of application Ser. No. 891,412, filed Mar. 29, 1978, now abandoned.

The present invention relates to a process for the preparation of 2-(2',2',2'-trihalogenoethyl)-4-halogenocyclobutan-1-ones of the formula I

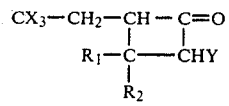

in which one of the radicals $R_1$ and $R_2$ is methyl and the other is hydrogen or methyl, or $R_1$ and $R_2$ together are an alkylene group having 2 to 4 carbon atoms, and X and Y are each chlorine or bromine.

The present invention also relates to the novel 2-(2',2',2'-trihalogenoethyl)-4-halogenocyclobutan-1-ones of the formula I which can be prepared by the process according to the invention and also to novel intermediates which can be used for their preparation.

It is known that α-halogenocycloalkanones are converted on heating in the presence of bases, such as alkali metal hydroxides and alkali metal alcoholates, to cycloalkanecarboxylic acids having the same number of carbon atoms, or esters thereof, with contraction of the ring (Favorski reaction). This reaction is the basis for an industrially important process for the preparation of cyclopropanecarboxylic acid derivatives and their esters having an insecticidal action, i.e. the pyrethyroids, from α-halogenocyclobutanones. However, it was not possible to use this process, which is technically simple to carry out, for the preparation of pyrethroids which are derived from 2-(2',2'-dihalogenovinyl)-cyclopropanecarboxylic acid, since corresponding α-halogenocyclobutanones suitable for the preparation of such cyclopropanecarboxylic acid derivatives were not available.

It has already been proposed to prepare α-halogenocyclobutanones by reacting a halogenoketene with an olefin. Processes of this type are described, for example, in German Offenlegungsschrift 2,539,048 and British Pat. No. 1,194,604 and also in J. Amer. Chem. Soc. 87, 5257–5259 (1965) and in Tetrahedron Letters No. 1, 135–139 (1966). This synthesis principle has not been used hitherto for the preparation of α-halogenobutanones, which are suitable as intermediates for the preparation of 2-(2',2'-dihalogenovinyl)-cyclopropane-carboxylic acids and their esters having an insecticidal action. This is in particular due to the fact that the synthesis possibilities which are conceivable on the basis of the abovementioned method, i.e.

(a) reaction of a halogenated olefin with a halogenoketene in accordance with the equation:

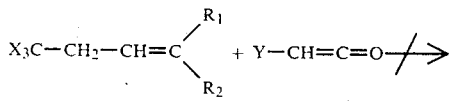

-continued

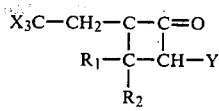

or

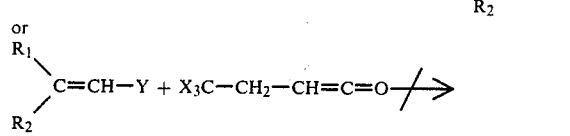

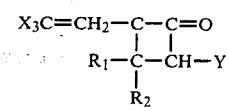

or (b) reaction of an unhalogenated olefin with a halogenoketene in accordance with the equation:

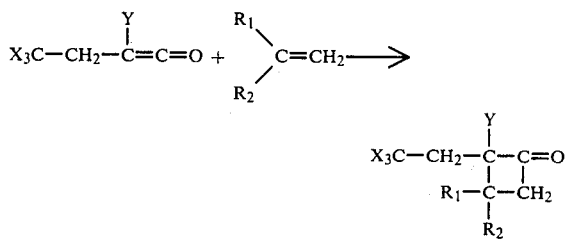

the symbols $R_1$, $R_2$, X and Y in the above equations being as defined under formula I, do not lead to the 2-(2',2',2'-trihalogenoethyl)-4-halogenocyclobutan-1-ones of the formula I, which are required as intermediates, since the reaction according to (a) does not take place because of the deactivation of the olefin which is associated with the substitution by halogen and the reaction according to (b) results in a 2-(2',2',2'-trihalogenoethyl)-2-halogenocyclobutan-1-one which cannot be converted into a 2-(2',2'-dihalogenovinyl)-cyclopropanecarboxylic acid, or an ester thereof, using an alkali metal hydroxide or alkali metal alcoholate.

The object on which the present invention is based is, therefore, to provide a process for the preparation of 2-(2',2',2'-trihalogenoethyl)-4-halogenocyclobutan-1-ones of the formula I which uses readily accessible starting materials and is simple to carry out.

A further object on which the present invention is based is to make available the 2-(2',2',2'-trihalogenoethyl)-4-halogenocyclobutan-1-ones of the formula I, which have not been known hitherto and which on heating with strong bases, such as alkali metal hydroxides or alkali metal alcoholates, give the corresponding 2-(2',2'-dihalogenovinyl)-cyclopropanecarboxylic acid derivatives, with contraction of the ring and, at the same time, the elimination of 2 mols of hydrogen halide, and also readily accessible intermediates which can be used for the preparation of α-halogenocyclobutanones of the formula I.

It has now been found that 2-(2',2',2'-trihalogenoethyl)-4-halogenocyclobutan-1-ones of the formula I can be prepared in a simple manner by reacting a 2,4,4,4-tetrahalogenobutyric acid chloride of the formula II

in which X and Y are as defined under formula I, in the presence of an organic base with an olefin of the formula III

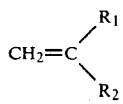  (III)

in which $R_1$ and $R_2$ are as defined under formula I, to give a 2-(2′,2′,2′-trihalogenoethyl)-2-halogenocyclobutan-1-one of the formula IV

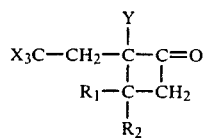  (IV)

in which $R_1$, $R_2$, X and Y are as defined under formula I, and then rearranging the latter, in the presence of a catalyst, into a 2-(2′,2′,2′-trihalogenoethyl)-4-halogenocyclobutan-1-one of the formula I.

The 2,4,4,4-tetrahalogenocutyric acid chlorides of the formula II are novel compounds. They can be prepared in a manner known per se by adding a carbon tetrahalide of the formula V

  (V)

in which X and Y are as defined under formula I, onto a compound of the formula VI $CH_2=CH-Z$  (VI)

in which Z is chlorocarbonyl, carboxyl, alkoxycarbonyl having 1 to 4 carbon atoms in the alkyl group, or cyano, and converting resulting compounds of the formula VII

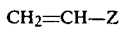  (VII)

in which X and Y are as defined under formula I and Z is carboxyl, alkoxycarbonyl or cyano, into compounds of the formula VII in which Z is chlorocarbonyl.

A further possibility for the preparation of 2,4,4,4-tetrahalogenobutyric acid chlorides of the formula II comprises adding a compound of the formula VIa

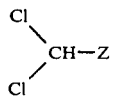  (VIa)

in which Z is as defined under formula VI, onto 1,1-dichloroethylene and converting resulting compounds of the formula VIIa

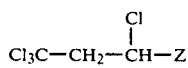  (VIIa)

in which Z is carboxyl, alkoxycarbonyl or cyano, into compounds of the formula VIIa in which Z is chlorocarbonyl.

When adding a carbon tetrahalide of the formula V onto an acrylic acid derivative of the formula VI and also when adding a dichloroacetic acid derivative of the formula VIa onto 1,1-dichloroethylene, the carbon tetrahalide of the formula V and, respectively, the dichloroacetic acid derivative of the formula VIa can be employed in the stoichiometric amount. Preferably, however, an excess of the carbon tetrahalide of the formula V or the dichloroacetic acid derivative of the formula VIa, for example an approximately 0.5-fold to 2-fold molar excess, is used and the carbon tetrahalide of the formula V can also serve as a solvent.

The adding of a carbon tetrahalide of the formula V onto a compound of the formula VI, and also the adding of a compound of the formula VIa onto 1,1-dichloroethylene, is carried out in the presence of catalysts. Suitable catalysts are metals of principal group VIII and sub-groups VIa, VIIa and Ib of the periodic system, for example iron, cobalt, nickel, ruthenium, rhodium, palladium, chromium, molybdenum, manganese and copper. These metals can be employed in the elementary form or in the form of compounds. Suitable compounds of these metals are, for example, oxides, halides, sulphates, sulphites, sulphides, nitrates, acetates, citrates, carbonates, cyanides and thiocyanates, and also complexes with ligands, such as phosphines, phosphites, benzoin, benzoyl- and acetyl-acetonates, nitriles, isonitriles and carbon monoxide.

Examples of compounds of the abovementioned metals which are suitable as catalysts are: copper-II oxide, iron-III oxide, the bromides, and in particular the chlorides, of Cu-I, Cu-II, Fe-II and Fe-III, and also the chlorides of ruthenium, rhodium, palladium, cobalt and nickel; Cu-II sulphate, Fe-II sulphate and Fe-III sulphate; Cu-II nitrate and iron-III nitrate; manganese-III acetate and copper-II acetate; copper-II stearate; iron-III citrate; Cu-I cyanide; ruthenium-II dichloro-tris-triphenylphosphine and rhodium tris-(triphenylphosphine) chloride; chromium acetylacetonate and nickel acetylacetonate, copper-II acetylacetonate, iron-III acetylacetonate, cobalt-II acetylacetonate and cobalt-III acetylacetonate, manganese-II acetylacetonate and copper-II benzoylacetonate; iron carbonyl-cyclopentadienyl complex; molybdenum carbonyl-cyclopentadienyl complex, chromium tricarbonyl-aryl complexes, ruthenium-II acetocomplex, chromium hexacarbonyl and molybdenum hexacarbonyl, nickel tetracarbonyl, iron pentacarbonyl, cobalt carbonyl and manganese carbonyl.

Mixtures of the said metals with metal compounds and/or other additives can also be used, such as copper powder in combination with one of the abovementioned copper compounds; mixtures of copper powder with lithium halides, such as lithium chloride, or with isocyanides, such as tert.-butyl isocyanide; mixtures of iron powder with iron-III chloride, if desired with the addition of carbon monoxide; mixtures of iron-III chloride and benzoin; mixtures of iron-II chloride or iron-III chloride and trialkyl phosphites; and mixtures of iron pentacarbonyl and iodine.

Preferred catalysts are iron-II salts and complexes and iron-III salts and complexes and also iron powder, but in particular copper powder, copper-I salts and complexes and copper-II salts and complexes, such as Cu-I chloride, Cu-II chloride, Cu-I bromide, Cu-II bromide, Cu-II acetylacetonate, Cu-II benzoylacetonate, Cu-II sulphate, Cu-II nitrate and Cu-I cyanide.

Very particularly preferred catalysts are copper powder, copper-I chloride and bromide and copper-II chloride and bromide, as well as mixtures thereof.

The said catalysts are generally used in amounts of about 0.01 to 10 mol%, preferably 0.1 to 5 mol%, based on the compound of the formula III or the 1,1-dichloroethylene.

The addition reactions are carried out in an organic solvent. Suitable organic solvents are those in which the catalysts are adequately soluble or which can form complexes with the catalysts, but which are inert towards the starting compounds. Examples of such solvents are alkylnitriles, especially those having 1—5 C atoms, such as acetonitrile, propionitrile and butyronitrile; 3-alkoxypropionitriles having 1 to 2 C atoms in the alkoxy moiety, such as 3-methoxypropionitrile and 3-ethoxypropionitrile; aromatic nitriles, in particular benzonitrile; aliphatic ketones having, preferably, a total of 3—8 C atoms, such as acetone, diethyl ketone, methyl isopropyl ketone, diisopropyl ketone and methyl tert.-butyl ketone; alkyl esters and alkoxyalkyl esters of aliphatic monocarboxylic acids having a total of 2-6 C atoms, such as methyl formate and ethyl formate, methyl acetate, ethyl acetate, n-butyl acetate and isobutyl acetate, and also 1-acetoxy-2-methoxyethane; cyclic ethers, such as tetrahydrofuran, tetrahydropyran and dioxane; dialkyl ethers having 1–4 C atoms in each alkyl moiety, such as diethyl ether, di-n-propyl ether and di-isopropyl ether; N,N-dialkylamides of aliphatic monocarboxylic acids having 1-3 C atoms in the acid moiety, such as N,N-dimethylformamide, N,N-dimethylacetamide, N,N-diethylacetamide and N,N-dimethylmethoxy-acetamide; ethylene glycol dialkyl ethers and diethylene glycol dialkyl ethers having 1–4 C atoms in each alkyl moiety, such as ethylene glycol dimethyl ether, ethylene glycol diethyl ether and ethylene glcyol di-n-butyl ether, and diethylene glycol diethyl ether and diethylene glycol di-n-butyl ether; and hexamethylphosphoric acid triamide (Hexametapol).

Preferred solvents are alkylnitriles having 2-5 C atoms and 3-alkoxypropionitriles having 1 or 2 C atoms in the alkoxy moiety, especially acetonitrile and 3-methoxypropionitrile.

The reaction temperature is in general not critical and can vary within wide limits. Preferably, the reaction temperatures are between about 60° and 200° C. and especially between about 80° to 170° C.

The compound of the formula VI or VIa which is used is preferably acrylic acid chloride or, respectively, dichloroacetyl chloride. By using these compounds the desired 2,4,4,4-tetrahalogenobutyric acid chlorides are obtained by a direct route in the pure form and in high yields. Further preferred compounds of the formulae VI and VIa are acrylic acid and dichloroacetic acid, respectively. The free 2,4,4,4-tetrahalogenobutyric acids obtained using these compounds can subsequently easily be converted, in a manner known per se, to the corresponding acid chlorides by reaction with inorganic acid chlorides, such as phosphorus trichloride, phosphorus pentachloride, phosphorus oxychloride, phosgene and thionyl chloride.

The esters or nitriles of a 2,4,4,4-tetrahalogenobutyric acid of the formula VII (Z=alkoxycarbonyl or cyano) which are obtained when compounds of the formula VI or VIa in which Z is alkoxycarbonyl or cyano are used are first hydrolyzed, in the presence of strong acids, such a concentrated hydrochloric acid, to the corresponding free 2,4,4,4-tetrahalogenobutyric acid and this is then converted to the corresponding acid chloride in the abovementioned manner.

The 2,4,4,4-Tetrahalogenobutyric acid chloride of Formula II wherein X is bromine and Y is chlorine, i.e. 2-chloro-4,4,4-tribromo butyryc acid chloride, can be prepared by reacting 4,4,4-tribromobutyric acid at first with an inorganic acid chloride to form 4,4,4-tribromobutyric acid chloride and subsequently chlorinating the latter in 2-position to form 2-chloro-4,4,4-tribromo-butyric acid chloride.

The tribromobutyric acid used as starting material can be obtained by reacting bromoform with acrylonitrile and subsequently hydrolysing the 4,4,4-tribromobutyronitrile formed (c.f. J.Amer.Chem. Soc. 67, 601–602 (1945)).

As inorganic acid chlorides there can be used phosphorus trichloride, phosphorus oxychloride phosgene, thionyl chloride and oxalyl chloride. The reaction of 4,4,4-tribromobutyric acid with the inorganic acid chloride is advantageously carried out in the presence of a catalytic amount of dimethylformamide. An excess of the inorganic acid chloride can be used as solvent.

The chlorination of 4,4,4-tribromobutyric acid chloride is carried out in the usual way. As chlorinating agents there can be used, for example, free chlorine or N-chlorosuccinimide. A preferred chlorinating agent is N:chlorosuccinimide. The chlorination can be performed immediately after the reaction of 4,4,4-tribromobutyric acid with the inorganic acid chloride in excess inorganic acid chloride as solvent without isolating the 4,4,4-tribromobutyric acid formed. However, a purer product is obtained if the 4,4,4-tribromobutyric acid chloride is isolated and the subsequent chlorination is carred out separately. The chlorination is performed at a temperature of from 40° to 90° C., preferably 60° to 70° C. Advantageously the chlorination is performed under irradiation with UV-light or in the presence of a compound producing free radicals, such as dibenzoylperoxide of azoisobutyronitril.

The reaction of the 2,4,4,4-tetrahalogenobutyric acid chlorides of the formula II with olefins of the formula III is advantageously carried out in the presence of an inert organic solvent. Suitable solvents are, for example, aromatic or aliphatic hydrocarbons, which can be halogenated, such as benzene, toluene, xylenes, chlorobenzene, dichloro- and trichloro-benzenes, n-pentane, n-hexane, n-octane, methylene chloride, chloroform, carbon tetrachloride, 1,1,2,2-tetrachloroethane and trichloroethylene. Further suitable solvents are cycloaliphatic hydrocarbons such as cyclopentane or cyclohexane, cycloaliphatic ketones such as cyclopentanone and cyclohexanone, and also aliphatic ketones, aliphatic and cyclic ethers, alkylnitriles and 3-alkoxypropionitriles having 1 or 2 carbon atoms in the alkoxy group, especially acetonitrile and 3-methoxypropionitrile.

Particularly suitable solvents are aliphatic, cycloaliphatic and aromatic hydrocarbons, in particular alkanes having 5 to 8 carbon atoms, benzene and toluene, and especially n-hexane and cyclohexane.

However, excess olefin of the formula III can also serve as the solvent.

Suitable organic bases, in the presence of which the reaction of a 2,4,4,4-tetrahalogenobutyric acid chloride of the formula II with an olefine of the formula III is carried out, are, for example, tertiary amines, in particular trialkylamines having 1 to 4 carbon atoms, and especially 2 to 4 carbon atoms, in each alkyl group, cyclic amines, such as pyridine, quinoline, and N-alkyl-pyrrolidines, N-alkyl-piperidines, N,N-dialkylpiperazines and N-alkyl-morpholines or dialkylanilines having 1 or 2 carbon atoms in each alkyl group, such as N-methyl-pyrrolidine, N-ethyl-piperidine, N,N'-dimethyl-piperazine, N-ethyl-morpholine and N,N-dimethylaniline, and also bicyclic amidines, such as 1,5-diazabicyclo[5.4.0]undec-5-ene and 1,5-diazabicyclo[4.3.0]non-5-ene, and bicyclic diamines, such as 1,4-diazabicyclo[2.2.2]octane.

The reaction of 2,4,4,4-tetrahalogenobutyric acid chlorides of the formula II with olefin of the formula III is preferably carried out in the presence of trialkyamines having 1 to 4 carbon atoms in each alkyl group. Particularly suitable bases are triethylamine and pyridine.

The organic base is employed in at least the equimolar amount, or in a slight excess, based on the 2,4,4,4-tetrahalogenobutyric acid chloride of the formula II.

The olefins of the formula III are likewise used in at least the equimolar amount, based on the 2,4,4,4-tetrahalogenobutyric acid chloride of the formula II. It is, however, generally advantageous to use an excess of the olefin, in which case the olefin can, as already mentioned, also serve as the solvent. When readily volatile olefins are used, the reaction can be carried out under pressure.

The olefins of the formula III are in particular those in which one of the radicals $R_1$ and $R_2$ is methyl and the other is hydrogen or methyl, or $R_1$ and $R_2$ together are an alkylene group having 2 to 3 carbon atoms, i.e. isobutylene, propene, methylenecyclopropane and methylenecyclobutane. Isobutylene and methylenecyclopropane are particularly preferred.

The reaction temperature can vary within wide limits. They are in general between 0° and 200° C. and preferably between 20° and 160° C.

The 2-(2',2',2'-trihalogenoethyl)-2-halogenocyclobutan-1-ones of the formula IV are also novel compounds. Catalysts which can be used for the rearrangement of the 2-(2',2',2'-trihalogenoethyl)-2-halogenocyclobutan-1-ones of the formula IV, which are first obtained, into 2-(2',2',2'-trihalogenoethyl)-4-cyclobutan-1-ones of the formula I are acids, bases or quaternary ammonium halides.

The rearrangement, according to the invention, of 2-(2',2',2'-trihalogenoethyl)-2-halogenocyclobutan-1-ones of the formula IV into 2-(2',2',2'-trihalogenoethyl)-4-halogenocyclobutan-1-ones of the formula I is unexpected and is not known in the case of cyclobutanones monohalogenated in the α-position. It is particularly surprising that no elimination of HX takes place at the trihalogenoethyl group when the rearrangement is carried out in the presence of a basic catalyst. The rearrangement proceeds with excellent, and frequently quantitative, yield.

The rearrangement, according to the invention, of 2-(2',2',2'-trihalogenoethyl)-2-halogenocyclobutan-1-ones of the formula IV into 2-(2',2',2'-trihalogenoethyl)-4-halogenocyclobutan-1-ones of the formula I is preferably carried out in the presence of basic catalysts. The basic catalysts are organic bases, such as primary, secondary and especially tertiary amines of the formula

in which $Q_1$ is alkyl having 1 to 8 carbon atoms, cycloalkyl having 5 to 6 carbon atoms, benzyl or phenyl and $Q_2$ and $Q_3$ independently of one another are hydrogen or alkyl having 1 to 8 carbon atoms. Suitable basic catalysts are, for example, triethylamine, tri-n-butylamine, tri-isopentylamine, tri-n-octylamine, N,N-dimethylcyclohexylamine, N,N-dimethylbenzylamine, N,N-dimethyl-2-ethylhexylamine, N,N-diethylaniline and also cyclic amines, such as pyridine, quinoline, lutidine, N-alkylmorpholines, such as N-methylmorpholines, N-alkylpiperidines, such as N-methyl- and N-ethyl-piperidine, N-alkylpyrrolidines, such as N-methyl- and N-ethyl-pyrrolidine, diamines, such as N,N,N',N'-tetramethylethylenediamine and N,N,N',N'-tetramethyl-1,3-diaminobutane, N,N'-dialkylpiperazines, such as N,N'-dimethylpiperazine, bicyclic amines, such as 1,4-diazabicyclo[2.2.2]octane, and bicyclic amidines, such as 1,5-diazabicyclo[5.4.0]undec-5-ene and 1,5-diazabicyclo[4.3.0]non-5-ene, and finally polymeric basic compounds, such as p-dimethylaminomethylpolystyrene.

Further suitable basic catalysts for the rearrangement, according to the invention, of a 2-(2',2',2'-trihalogenoethyl)-2-halogenocyclobutan-1-one of the formula IV into a 2-(2',2',2'-trihalogenoethyl)-4-halogenocyclobutan-1one of the formula I are phosphines, especially trialkylphosphines, for example tributylphosphine.

Acid catalysts which can be used for the rearrangement of 2-(2',2',2'trihalogenoethyl)-2-halogenocyclobutan-1-ones of the formula IV into 2-(2',2',2'-trihalogenoethyl)-4-halogenocyclobutan-1-ones of the formula I are inorganic or organic proton acids. Suitable inorganic proton acids are, for example, hydrogen halide acids, such as hydrogen chloride, hydrogen bromide, hydrogen fluoride and hydrogen iodide, nitric acid, phosphoric acid and sulphuric acid. Preferred inorganic proton acids are hydrogen halide acids.

If acids or bases are employed in excess, they can also serve as solvents.

Furthermore, salts of proton acids, especially hydrogen halide acids, with ammonia or a nitrogen-containing organic base, and also quaternary ammonium halides, quaternary phosphonium halides and sulphonium halides can be employed. Suitable nitrogen-containing organic bases are aliphatic, cycloaliphatic, araliphatic and aromatic primary, secondary and tertiary amines, as well as heterocyclic nitrogen bases. Examples are: primary aliphatic amines having up to 12 C atoms, such as methylamine, ethylamine, n-butylamine, n-octylamine, n-dodecylamine, hexamethylenediamine, cyclohexylamine and benzylamine; secondary aliphatic amines having up to 12 C atoms, such as dimethylamine, diethylamine, di-n-propylamine, dicyclohexylamine, pyrrolidine, piperidine, piperazine and morpholine; tertiary aliphatic amines, especially trialkylamines having 1-4 C atoms in each alkyl moiety, such as triethylamine, tri-n-butylamine, N-methylpyrrolidine, N-methylmorpholine, 1,4-diazabicyclo[2.2.2]octane and quinuclidine; substituted or unsubstituted primary, secondary and tertiary aromatic amines, such as aniline, toluidine, naphthylamine, N-methylaniline, diphenylamine and N,N-diethylaniline; and also pyridine, picoline, indoline and quinoline.

Quaternary phosphonium halides which can be used are, for example: hexadecyltributylphosphonium bromide and methyl- and ethyl-triphenylphosphonium bromide; and a sulphonium halide which can be used is, for example, trimethylsulphonium iodide.

Preferred salts are those of the formula

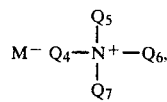

in which M is fluorine, bromine or iodine and especially chlorine, $Q_4$ is hydrogen, alkyl having 1–18 C atoms, cyclohexyl, benzyl, phenyl or naphthyl and $Q_5$, $Q_6$ and $Q_7$ independently of one another are hydrogen or alkyl having 1–18 C atoms, and also N-alkyl-pyridinium halides having 1–18 C atoms in the alkyl, especially the corresponding chlorides.

Examples of such salts are: ammonium chloride, ammonium bromide, methylamine hydrochloride, cyclohexylamine hydrochloride, aniline hydrochloride, dimethylamine hydrochloride, di-isobutylamine hydrochloride, triethylamine hydrochloride, triethylamine hydrobromide, tri-n-octylamine hydrochloride, benzyldimethylamine hydrochloride, tetramethylammonium chloride, bromide and iodide, tetraethylammonium chloride, bromide and iodide, tetra-n-propylammonium chloride, bromide and iodide, tetra-n-butylammonium chloride, bromide and iodide, trimethyl-hexadecylammonium chloride, benzyldimethylhexadecylammonium chloride, benzyldimethyltetradecylammonium chloride, benzyl-trimethyl-, -triethyl- and -tri-n-butyl-ammonium chloride, n-butyl-tri-n-propylammonium bromide, octadecyltrimethylammonium bromide, phenyltrimethylammonium bromide or chloride and hexadecylpyridinium bromide and chloride.

Additional co-catalysts which can be used are alkali metal halides, such as potassium iodide, sodium iodide, lithium iodide, potassium bromide, sodium bromide, lithium bromide, potassium chloride, sodium chloride, lithium chloride, potassium fluoride, sodium fluoride and lithium fluoride.

These co-catalysts catalyze the reaction even in the absence of the above ammonium salts, but additions of open-chain or macrocyclic polyethers (crown ethers) are then advantageous for a rapid course of reaction. Examples of such crown ethers are: 15-crown-5, 18-crown-6, dibenzo-18-crown-6, dicyclohexyl-18-crown-6 and 5,6,14,15-dibenzo-7,13-diaza-1,4-dioxa-cyclopentadeca-5,14-diene.

The amount of catalyst employed can vary within wide limits. In some cases it suffices if the catalyst is present in traces. In general, however, the catalyst is preferably employed in an amount of about 0.1 to 15 percent by weight, based on the compound of the formula VI.

The rearrangement can be carried out either in the melt or in an inert organic solvent. The reaction temperatures for the rearrangement in the melt are in general between about 60° and 150° C. and especially about 80° and 130° C.

Suitable catalysts for the rearrangement in the melt are, in particular, the abovementioned organic bases, especially trialkylamines having 1–8 C atoms in each alkyl moiety; and also salts of hydrogen halide acids with ammonia or organic nitrogen-containing bases, such as trialkylamine hydrochlorides and hydrobromides having 1–8 C atoms in each alkyl moiety, and very particularly tetraalkylammonium halides, in particular tetraalkylammonium chlorides, bromides and iodides, having 1–18 C atoms in each alkyl moiety.

Examples of suitable inert organic solvents are aliphatic, cycloaliphatic or aromatic hydrocarbons, which can be nitrated or halogenated, such as n-hexane n-pentane, cyclohexane, benzene, toluene, xylenes, nitrobenzene, chloroform, carbon tetrachloride, trichloroethylene, 1,1,2,2-tetrachloroethane, nitromethane, chlorobenzene, dichlorobenzenes and trichlorobenzenes; lower aliphatic alcohols, for examples those having up to 6 C atoms, such as methanol, ethanol, propanol, isopropanol, butanols and pentanols; aliphatic diols, such as ethylene glycol and diethylene glycol; ethylene glycol monoalkyl ethers and diethylene glycol monoalkyl ethers having, in each case, 1–4 C atoms in the alkyl moieties, such as ethylene glycol monomethyl ether and ethylene glycol monoethyl ether, diethylene glycol monomethyl ether and diethylene glycol monoethyl ether; cyclic amides, such as N-methyl-2-pyrrolidone, N-acetyl-2-pyrrolidone and N-methyl-ε-caprolactam; amides of carbonic acid, such as tetramethylurea and dimorpholinocarbonyl; amides of phosphorous acid, of phosphoric acid, of phenylphosphonic acid or of aliphatic phosphonic acids having 1–3 C atoms in the acid moiety, such as phosphoric acid triamide, phosphoric acid tris-(dimethylamide), phosphoric acid trimorpholide, phosphoric acid tripyrrolinide, phosphoric acid bis-(dimethylamide)-morpholide, phosphoric acid dimethylamide-diethylamide-morpholide, phosphorous acid tris-(dimethylamide) and the tetramethyldiamide of methanephosphonic acid; amides of sulphuric acid and of aliphatic or aromatic sulphonic acids, such as tetramethylsulphamide, the dimethylamide of methanesulphonic acid or p-toluenesulphonic acid amide; sulphur-containing solvents, such as organic sulphones and sulphoxides, for example dimethylsulphoxide and sulpholane; and aliphatic and aromatic nitriles, 3-alkoxypropionitriles, aliphatic ketones, alkyl and alkoxyalkyl esters of aliphatic monocarboxylic acids, cyclic ethers, dialkyl ethers, N,N-disubstituted amides of aliphatic monocarboxylic acids and ethylene glycol dialkyl ethers and diethylene glycol dialkyl ethers of the type mentioned under process stage 1).

For the rearrangement in the presence of an acid catalyst, polar solvents are advantageously used, especially lower alcohols, such as methanol, ethanol and butanols, N,N-dialkylamides of aliphatic monocarboxylic acids having 1–3 C atoms in the acid moiety, especially N,N-dimethylformamide, or dialkylsulphoxides, such as dimethylsulphoxide.

In aprotic, strongly polar solvents, such as the abovementioned N,N-disubstituted amides of aliphatic monocarboxylic acids, cyclic amides, amides of carbonic acid, amides of phosphorous acid, of phosphoric acid, of phenylphosphonic acid or of aliphatic phosphonic acids, amides of sulphuric acid or of aliphatic or aromatic sulphonic acids, and also dialkylsulphoxides, such as dimethylsulphoxide, the reaction also proceeds without the addition of base or acid. In these cases, the solvent acts as the catalyst.

In general, however, when the rearrangement is carried out in the presence of an inert organic solvent a catalyst is added, preferably an organic base having a pK_a value of more than 9, especially trialkylamines having 1-8 C atoms in each alkyl moiety, such as triethylamine, tri-n-butylamine and tri-n-octylamine; and also hydrogen halide acids, especially HCl and HBr, and tetraalkylammonium halides, especially tetraalkylammonium chlorides, bromides and iodides having 1-18 C atoms in each alkyl moiety.

Particularly preferred solvents are aliphatic alcohols having 1-4 C atoms, toluene, xylenes, chlorobenzene, dioxane, acetonitrile, 3-methoxypropionitrile, ethylene glycol diethyl ether and di-isopropyl ketone.

The reaction temperatures for the rearrangement in the presence of an inert organic solvent are in general between about 0° and 150° C. and preferably between about 80° and 130° C.

By means of the process according to the invention, novel 2-(2',2',2'-trihalogenoethyl)-4-halogeno-cyclobutan-1-ones of the formula I, which are substituted in the 3-position and are suitable as intermediates for the preparation of 2-(2',2'-dihalogenovinyl)-cyclopropanecarboxylic acid derivatives substituted in the 3-position, are available in a simple manner and in good yield, using readily accessible starting materials. The process according to the invention is especially suitable for the preparation of 2-(2',2',2'-trichloroethyl)-4-halogenocyclobutan-1-ones of the formula I which are substituted in the 3-position. The course of the process according to the invention is extremely surprising and completely unforeseeable, since, when a 2,4,4,4-tetrahalogenobutyric acid chloride of the formula II, or a halogenoketene formed therefrom in situ by the elimination of hydrogen chloride, is reacted with an olefin of the formula III, a 2-(2',2',2'-trihalogenoethyl)-2-halogenocyclobutan-1-one of the formula IV, which is unsuitable for further conversion into a 2-(2',2'-dihalogenovinyl)-cyclopropanecarboxylic acid derivative substituted in the 3-position, is first formed and this is then converted, by a novel rearrangement, not hitherto observed in the case of cyclobutanones, monohalogenated in the α-position, into a 2-(2',2',2'-trihalogenoethyl)-4-halogenocyclobutan-1-one of the formula I, which is suitable for further conversion into a 2-(2',2'-dihalogenovinyl)-cyclopropanecarboxylic acid derivative substituted in the 3-position.

The 2-(2',2'-dihalogenovinyl)-cyclopropanecarboxylic acids substituted in the 3-position, and their esters having an insecticidal action, which can be prepared using novel 2-(2',2',2'-trihalogenoethyl)-4-chlorocyclobutan-1-ones of the formula I as the starting materials, can be described by the following formula VIII:

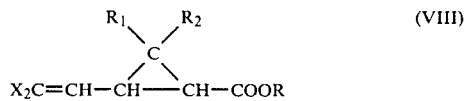

in which X, $R_1$ and $R_2$ are as defined under formula I and R is hydrogen, alkyl having 1 to 4 carbon atoms or a group of the formula IX

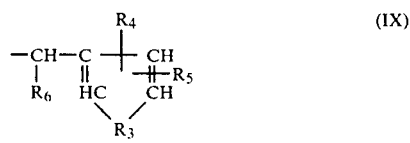

in which $R_3$ is oxygen, sulphur or a vinylene group, $R_4$ is hydrogen, alkyl having 1 to 4 carbon atoms, benzyl, phenoxy or phenylmercapto, $R_5$ is hydrogen or an alkyl group having 1 to 4 carbon atoms and $R_6$ is hydrogen, cyano or ethynyl, or, if one of the radicals $R_1$ and $R_2$ is methyl and the other is hydrogen or methyl, $R_3$ is the vinylene group, $R_4$ is phenoxy and $R_5$ is hydrogen, also alkyl having 1 to 5 carbon atoms.

The 2-(2',2'-dihalogenovinyl)-cyclopropanecarboxylic acid derivatives of the formula VIII in which R is a group of the formula IX are suitable for combating diverse animal on plant pests, especially insects. The properties, fields of application and use forms of these active compounds are described in the literature (c.f., for example, Nature, 246, 169-170 (1973); Nature, 248, 710-711 (1974); Proceedings 7th British Insecticide and Fungicide Conference, 721-728 (1973); Proceedings 8th British Insecticide and Fungicide Conference, 373-78 (1975); J. Agr. Food Chem. 23, 115 (1973); U.S. Pat. No. 3,961,070; and German Offenlegungsschriften Nos. 2,553,991, 2,439,177, 2,326,077 and No. 2,614,648).

The conversion of 2-(2',2',2'-trihalogenoethyl)-4-halogenocyclobutan-1-ones of the formula I into 2-(2',2'-dihalogenovinyl)-cyclopropanecarboxylic acid derivatives of the formula VIII is carried out in a manner known per se, by heating in the presence of suitable bases. Examples of suitable bases are alkali metal hydroxides and alkaline earth metal hydroxides, such as sodium hydroxide, potassium hydroxide, calcium hydroxide and barium hydroxide. Alkali metal carbonates and bicarbonates and alkaline earth metal carbonates and bicarbonates, such as calcium carbonate, barium carbonate, potassium carbonate, sodium carbonate, sodium bicarbonate and potassium bicarbonate, can also be used as bases. Further suitable bases are alcoholates derived from the radical R according to the above definition, especially the corresponding sodium alcoholates and potassium alcoholates. The use of such alcoholates has the advantage that the corresponding ester is obtained direct, whilst when alkali metal hydroxides and alkaline earth metal hydroxides are used, the salts of these bases with the 2-(2',2'-dihalogenovinyl)-cyclopropanecarboxylic acid formed are first obtained. These salts can, however, also be converted into esters in a simple manner which is known per se, for example by converting them into the corresponding acid chloride and reacting the latter with an alcohol derived from the radical R.

Depending on the nature of the base used, the conversion of a 2-(2',2',2'-trihalogenoethyl)-4-halogenocyclobutan-1-one of the formula I into a 2-(2',2'-dihalogenovinyl)-cyclopropanecarboxylic acid derivative of the formula VIII is advantageously carried out in an aqueous, aqueous-organic or organic medium. When the base used is an alkali metal carbonate or alkaline earth metal carbonate, the reaction is carried out in an aqueous or aqueous-organic medium. The reaction in the presence of alkali metal hydroxides or alkaline earth metal hydroxides and alkali metal bicarbonates is also advantageously carried out in an aqueous or aqueous-organic medium. In this case, the free 2-(2',2'-dihalogenovinyl)-cyclopropanecarboxylic acids of the formula VIII (R=H) are obtained after acidifying the reaction mixture, for example by adding concentrated hydrochloric acid.

Suitable solvents for the conversion of 2-(2',2',2'-trihalogenoethyl)-4-halogenocyclobutan-1-ones of the formula I into 2-(2',2'-dihalogenovinyl)-cyclopropanecarboxylic acid derivatives of the formula VIII in an aqueous-organic or organic medium are lower alcohols, for example those having 1 to 6 carbon atoms, benzyl alcohol, aliphatic or cyclic ethers, such as diethyl ether, di-n-propyl ether, diisopropyl ether, tetrahydrofuran and dioxane, and also aliphatic, cycloaliphatic or aromatic hydrocarbons, such as n-pentane, n-hexane, cyclohexane, benzene, toluene and xylenes.

The conversion of 2-(2',2',2'-trihalogenoethyl)-4-halogenocyclobutan-1-ones of the formula I to 2-(2',2'-dihalogenovinyl)-cyclopropanecarboxylic acid derivatives of the formula VIII is generally carried out at the boiling point of the reaction medium chosen. Reaction temperatures of between 40° and 120° C. are particularly suitable.

When 2-(2',2',2'-trihalogenoethyl)-4-halogenocyclobutan-1-ones of the formula I are converted into 2-(2',2'-dihalogenovinyl)-cyclopropanecarboxylic acid derivatives of the formula VIII, the corresponding 2-(2',2',2'-trihalogenoethyl)-cyclopropanecarboxylic acid derivatives of the formula X

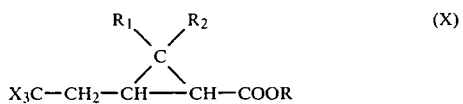

in which R, $R_1$, $R_2$ and X are as defined, are formed as intermediates. These products can be isolated if the reaction temperature is kept below 40° C. and/or a less than equivalent amount of base is used. Above 40° C., these intermediates are converted to the corresponding 2-(2',2'-dihalogenovinyl)-cyclopropanecarboxylic acid derivatives of the formula VIII on the addition of further base, with the elimination of HX.

The 2-(2',2',2'-trihalogenoethyl)-cyclopropanecarboxylic acid derivatives of the formula X can also be prepared photochemically from 2-(2',2',2'-trihalogenoethyl)-4-halogenocyclobutan-1-ones of the formula I, by irradiation with UV light, if necessary with the addition of conventional sensitisers (for example ketones, such as acetone, cyclohexanone, benzophenone, acetophenone and higher alkylaryl ketones, thioxanthone and the like), in the presence of reagents containing hydroxyl groups, which at the same time can serve as solvents. Examples of reagents containing hydroxyl groups are alkanols, such as methanol, ethanol and the like, and in particular water.

The process according to the invention is illustrated in more detail by the following examples.

EXAMPLE 1

(a) Preparation of 2,4,4,4-tetrachlorobutyric acid chloride 452.5 g (5 mols) of acrylic acid chloride (technical grade purity), 1.5 liters of carbon tetrachloride, 1.5 liters of acetonitrile and 30 g of copper-I chloride are kept at 115° C. for 24 hours. The reaction mixture is filtered to give a clear filtrate and the latter is evaporated under a waterpump vacuum. The residue is distilled. This gives 922 g (76% of theory) of 2,4,4,4-tetrachlorobutyric acid chloride; boiling point 78°–80° C./11 mm Hg.

IR spectrum (CHCl$_3$) in cm$^{-1}$: 1780 (C=O). NMR spectrum (100 MHz, CDCl$_3$) in ppm: 3.16–3.94 (m, 2H, CH$_2$); 4.84–4.96 (m, 1H, CH).

2,4,4,4-Tetrachlorobutyric acid chloride can also be prepared as follows:

90.5 g (1 mol) of acrylic acid chloride, 0.5 liter of carbon tetrachloride, 0.2 liter of butyronitrile and 3 g of copper powder are heated at 115° C. for 20 hours. The reaction mixture is filtered, the filtrate is evaporated and the residue is distilled. This gives 167.8 g (69% of theory) of 2,4,4,4-tetrachlorobutyric acid chloride; melting point: 80°–81° C./12 mm Hg. The spectroscopic data are identical to those of the 2,4,4,4-tetrachlorobutyric acid chloride prepared according to paragraph 1.

If the copper powder is replaced by copper-I chloride and the butyronitrile is replaced by 3-methoxypropionitrile and the procedure is otherwise identical, 2,4,4,4-tetrachlorobutyric acid chloride is obtained in a yield of 71% of theory.

226 g (1mol) of 2,4,4,4-tetrachlorobutyric acid [prepared in accordance with Israeli Patent Specification 18,771=CA, 63, 13089e (1965)], 600 g of thionyl chloride and 1 ml of N,N-dimethylformamide are warmed at 50° C. for 2 hours and at 75° C. for 2 hours. After evaporating off the excess thionyl chloride, the residue is distilled. This gives 227.6 g (93% of theory) of 2,4,4,4-tetrachlorobutyric acid chloride; boiling point 90°–91° C./15 mm Hg.

145.9 g (1.5 mols) of 1,1-dichloroethylene, 147.4 g (1 mol) of dichloroacetyl chloride, 200 ml of acetonitrile and 3 g of copper-I chloride are heated at 130° C. for 8 hours. The reaction mixture is evaporated and the residue is subjected to fractional distillation. This gives 2,4,4,4-tetrachlorobutyric acid chloride in the form of a colorless liquid; boiling point 78°–80° C./11 mm Hg. The spectroscopic data of the substance obtained are identical to those of the 2,4,4,4-tetrachlorobutyric acid chloride prepared according to paragraph 1.

(b) Preparation of 2-chloro-2-(2',2',2'-trichloroethyl)-3,3-dimethylcyclobutan-1-one 280 g of isobutylene are injected into 122 g (0.5 mol) of 2,4,4,4-tetrachlorobutyric acid chloride in 600 ml of cyclohexane, in an autoclave. A solution of 51 g (0.5 mol) of triethylamine in 500 ml of cyclohexane is pumped in at 65° C. in the course of 4 hours. The reaction mixture is then kept at 65° C. for a further 3 hours. The hydrochloride of triethylamine, which has precipitated, is filtered off and the filtrate is evaporated. The crystals thus obtained are filtered off. This gives 79.4 g (60% of theory) of 2-chloro-2-(2',2',2'-trichloroethyl)-3,3-dimethylcyclobutan-1-one with a melting point of 75°–76° C.

IR spectrum (CHCl$_3$) in cm$^{-1}$: 1805 (C=O).

$^1$H NMR spectrum (100 MHz, CDCl$_3$) in ppm: 1.42 and 1.45 (in each case 1s, 6H and in each case 1 CH$_3$); 2.91–3.28 (m, 2H, CH$_2$); 3.37–3.76 (m, 2H, CH$_2$).

$^{13}$C NMR spectrum (CDCl$_3$) in ppm: 196 (s, CO); 95.3 (s, CH$_3$); 80.8 (s, C-2); 57.0 (t, CH$_2$); 56.4 (t, CH$_2$); 37.9 (s, C-3); 25.1 (q, CH$_3$); 28.8 (q, CH$_3$).

Elementary analysis for C$_8$H$_{10}$Cl$_4$O (molecular weight 263.98): calculated C 36.40%; H 3.82%; O 6.02%; Cl 53.72%. found C 36.4%; H 3.9%; O 6.2%; Cl 53.5%.

(c) Preparation of 2-(2',2',2'-trichloroethyl)-3,3-dimethyl-4-chlorocyclobutan-1-one 132 g (0.5 mol) of the resulting 2-chloro-2-(2',2',2'-trichloroethyl)-3,3-dimethylcyclobutan-1-one are dissolved in 700 ml of toluene, 1 ml of triethylamine is added and the mixture is boiled under reflux. After a reaction time of 13 hours, a further 1 ml of triethylamine is added and the mixture is boiled for a further 7 hours. After cooling, the reaction mixture is washed, first with dilute hydrochloric acid and then with water, dried and evaporated. The solidified residue (124 g; 94% of theory), which according to thin layer chromatography is a single compound, is crystallized from n-hexane. This gives 105.8 g of 2-(2′,2′,2′-trichloroethyl)-3,3-dimethyl-4-chlorocyclobutan-1-one; melting point 56°–57° C.

IR spectrum (CHCl₃) in cm⁻¹: 1800 (c=O).

¹H NMR spectrum (100 MHz, CDCl₃) in ppm: 4.77 (d, J=2 Hz, 1H, H on C-4); 3.47 (m, 1H, H on C-2); 2.73–3.26 (m, 2H, CH₂); 2.63 (s, 3H, CH₃); 1.14 (s, 3H, CH₃).

¹³C-NMR spectrum (CDCl₃) in ppm: 197.0 (s, CO); 97.8 (s, CCl₃); 69.4 (d, C-4); 60.6 (d, C-2); 49.5 (t, CH₂-CCl₃); 36.8 (s, C-3); 27.4 (q, CH₃); 18.6 (q, CH₃).

Elementary analysis for C₈H₁₀Cl₄O (molecular weight 263.98): calculated C 36.40%; H 3.82%; O 6.02%; Cl 53.72%. found C 36.6%; H 3.8%; O 6.2%; Cl 53.6%.

The above compound can also be prepared as follows: 2.64 g (0.01 mol) of 2-chloro-2-(2′,2′,2′-trichloroethyl)-3,3-dimethylcyclobutanone and 220 mg (0.0008 mol) of tetra-n-butylammonium chloride are stirred for 6.5 hours at 124° C. The cooled melt is boiled up with hot n-hexane and filtered to give a clear filtrate. As the filtrate cools, 2.19 g (83% of theory) of 2-(2′,2′,2′-trichloroethyl)-3,3-dimethyl-4-chlorocyclobutanone with a melting point of 53°–56° C. precipitate.

(d) Preparation of 2-(2′,2′-dichlorovinyl)-3,3-dimethylcyclopropane-1-carboxylic acid 13.2 g (0.05 mol) of 2-(2′,2′,2′-trichloroethyl)-3,3-dimethyl-4-chlorocyclobutan-1-one are added to 150 ml of 10% strength sodium hydroxide solution and the mixture is stirred intensively. After 5 minutes a clear solution has formed and this is warmed at 100° C. (bath temperature) for 1 hour. The reaction solution is washed with diethyl ether, acidified with concentrated hydrochloric acid, with cooling, and extracted with diethyl ether. The ether phase is washed with water, dried over magnesium sulphate and evaporated. According to the NMR spectrum, the solid residue (10.35 g) consists of 80% by weight of cis-2-(2′,2′-dichlorovinyl)-3,3-dimethylcyclopropane-1-carboxylic acid and 20% by weight of trans-2-(2′,2′-dichlorovinyl)-3,3-dimethylcyclopropane-1-carboxylic acid. Crystallization from n-hexane gives the pure cis-acid; melting point 85°–87° C.

IR spectrum (CHCl₃) in cm⁻¹: 1710 (CO), 1625 (C=C).

NMR spectrum (100 MHz, CDCl₃/D₂O) in ppm: 1.30 (s, 6H, 2×CH₃); 1.85 (d, J=8.5 Hz, 1H, HC-1); 2.02–2.19 (m, 1H, HC-2); 6.17 (d, J=8 Hz, 1H, CH=CCl₂).

EXAMPLE 2

421 g of propylene, 244 g (1 mol) of 2,4,4,4-tetrachlorobutyric acid chloride and 1.25 liters of cyclohexane are initially introduced into a 6.3 liter autoclave. A solution of 101 g (1 mol) of triethylamine in 1 liter of cyclohexane is pumped in at 50° C. in the course of 4 hours and the reaction mixture is then kept at 50° C. for 3 hours. The reaction mixture is filtered and the resulting filtrate is washed with dilute hydrochloric acid and then with water, dried over magnesium sulphate and evaporated. The residue is crystallised from n-hexane. This gives 77.2 g of 2-chloro-2-(2′,2′,2′-trichloroethyl)-3-methylcyclobutan-1-one; melting point 80°–81° C.

IR spectrum (CHCl₃) in cm⁻¹: 1785 (CO).

¹H NMR spectrum (100 MHz, CDCl₃) in ppm: 3.28–3.73 (m, 3H); 2.65–2.95 (m, 2H); 1.43 (d, J=6.5 Hz, 3H, CH₃).

¹³C NMR spectrum (CDCl₃) in ppm: 196.5 (s, CO); 95.1 (s, CCl₃); 77.8 (s, C-2); 55.3 (t, CH₂-CCl₃); 50.9 (t, C-4); 38.1 (d, C-3); 15.8 (q, CH₃).

1 ml of triethylamine is added to 50 g (0.2 mol) of the resulting 2-chloro-2-(2′,2′,2′-trichloroethyl)-3-methylcyclobutan-1-one in 500 ml of toluene and the mixture is stirred for 18 hours at a bath temperature of 120° C. After cooling, the reaction mixture is filtered to give a clear filtrate and the filtrate is washed, first with dilute hydrochloric acid and then with water, boiled up briefly with active charcoal, filtered again and evaporated. Distillation of the residue gives 38.7 g (77% of theory) of 2-(2′,2′,2′-trichloroethyl)-3-methyl-4-chlorocyclobutan-1-one; boiling point 130°–131° C./12 mm Hg.

IR spectrum (CHCl₃) in cm⁻¹: 1805 (CO).

NMR spectrum (100 MHz, CDCl₃) in ppm: 1.20 (d, J=7 Hz, 0.6H, CH₃); 1.46 (d, J=7 Hz, 0.45H, CH₃); 1.66 (d, J=6.5 Hz, 1.95H, CH₃); 2.1–3.5 (m, 4H); 4.55 (dd, J=8 and 2 Hz, 0.65H, CH); 5.00 (dd, J=9 and 2.5 Hz, 0.15 H, CH); 5.15 (dd, J=9 and 1.5 Hz, 0.2H, CH).

According to the NMR spectrum and the gas chromatogram, the compound consists of 3 stereoisomers in a weight ratio of 13:4:3.

10.5 g of the resulting 2-(2′,2′,2′-trichloroethyl)-3-methyl-4-chlorocyclobutan-1-one are stirred with 100 ml of 10% strength sodium hydroxide solution for 50 minutes. The solution which has formed is then heated at 100° C. for 1 hour. The reaction mixture is then washed with diethyl ether and carefully acidified with concentrated hydrochloric acid. It is then extracted with diethyl ether. The ether extract is washed with water, dried over magnesium sulphate and evaporated. This gives 2-(2′,2′-dichlorovinyl)-3-methylcyclopropane-1-carboxylic acid; melting point 75°–78° C. (recrystallised from n-hexane).

IR spectrum (KBr) in cm⁻¹: 1685 (C=O), 1625 (C=C).

NMR spectrum (100 MHz, CDCl₃/D₂O) in ppm: 1.25 (d, J=5.5 Hz, 3H, CH₃); 1.54–2.18 (m, 3H); 3.96 (d, J=8 Hz, 1H, CH-CCl₂).

EXAMPLE 3

A solution of 25.3 g (0.25 mol) of triethylamine in 50 ml of n-hexane is added dropwise, in the course of 7 hours, with stirring, to a solution, which is kept under reflux, of 25 g (0.37 mol) of methylenecyclobutane and 61.1 g (0.25 mol) of 2,4,4,4-tetrachlorobutyric acid chloride in 200 ml of n-hexane. After the reaction mixture has been stirred under reflux for a further 2 hours, it is freed, whilst still hot, from the ammonium salt formed, by filtration. The filtrate is concentrated to about ⅓ its volume. On cooling, 1-chloro-1-(2′,2′,2′-trichloroethyl)-spiro[3.3]heptan-2-one of the formula

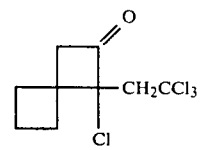

precipitates in a crystalline form; melting point 93°–94° C.

IR spectrum (CCl₄) in cm⁻¹: 1790 (C=O).

NMR spectrum (100 MHz, CDCl₃) in ppm: 1.70–2.80 (m, 6H); 3.15–3.60 (m, 4H).

A solution of 27.6 g (0.1 mol) of the resulting 1-chloro-1-(2',2',2'-trichloroethyl)spiro[3.3]heptan-2-one in 100 ml of toluene, together with 0.93 g (5 mmols) of tributylamine, is refluxed for 9 hours. The reaction mixture is then evaporated and the residue is distilled in vacuo. This gives 1-chloro-3-(2',2',2'-trichloroethyl)-spiro[3.3]heptan-2-one of the formula

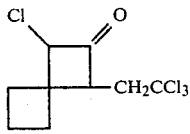

in the form of a slightly yellowish oil; boiling point 85°–90° C./0.005 mm Hg; $n_D^{20}$ = 1.5242.

IR spectrum (film) in cm$^{-1}$: 1795 (C=O).

NMR spectrum (100 MHz, CDCl$_3$) in ppm: 1.80–3.85 (m, 9H); 4.68, 4.93 (each one d, together 1H).

11.0 g (40 mmols) of the resulting 1-chloro-3-(2',2',2'-trichloroethyl)spiro[3.3]heptan-2-one are stirred together with 95 ml (about 240 mmols) of 10% strength sodium hydroxide solution for 6 hours at 95° C. After cooling, the mixture is washed with several portions of diethyl ether, acidified with sulphuric acid and extracted with diethyl ether. The ether extracts are evaporated after drying over sodium sulphate. A small amount of strongly polar impurities is eliminated by filtering the residue from ten times the amount by weight of silica gel (eluant n-hexane/diethyl ether in a volume ratio of 1:1). After concentrating the filtrate, 2-(2',2'-dichlorovinyl)spiro[2.3]hexane-1-carboxylic acid of the formula

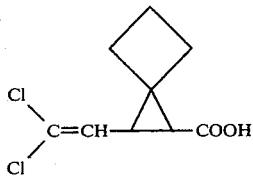

is obtained in the form of a 2:1 cis/trans mixture; melting point 121°–28° C.

IR spectrum (CCl$_4$) in cm$^{-1}$: 1705 (C=O).

NMR spectrum (100 MHz, CDCl$_3$) in ppm: 1.60–2.60 (m, 8H); 5.34, 5.97 (each one d, together 1H); 11.80–11.50 (broad s, 1H).

EXAMPLE 4

280 g of isobutylene are injected into 122 g (0.5 mol) of 2,4,4,4-tetrachlorobutyric acid chloride in 600 ml of cyclohexane, in an autoclave. 51 g (0.5 mol) of triethylamine in 500 ml of cyclohexane are pumped in at 65° C. in the course of 4 hours. The reaction mixture is then kept at 65° C. for 3 hours and then heated at 125° C. for 18 hours. During this time, 2.0 g of triethylamine in 50 ml of cyclohexane are pumped in every 3 hours. The reaction mixture is poured onto ice, acidified with hydrochloric acid and extracted with cyclohexane. The evaporated extract is filtered in toluene/cyclohexane (1:1 mixture by volume) through 1 kg of silica gel in order to remove strongly polar impurities. The filtrate is evaporated and the residue is crystallized from n-hexane. This gives 31.8 g of 2-(2',2',2'-trichloroethyl)-3,3-dimethyl-4-chlorocyclobutan-1-one; melting point 56°–57° C.

EXAMPLE 5

(a) 26.1 g (99 mmols) of 2-(2',2',2'-trichloroethyl)-3,3-dimethyl-4-chlorocyclobutanone are added to 260 ml of a 10% strength sodium hydroxide solution, at 11° C., with stirring. The temperature rises to 28° C. in the course of 2.4 hours and then falls to 20° C. in the course of a further 2 hours. The reaction mixture is diluted with 200 ml of water, washed with diethyl ether, rendered strongly acid with concentrated hydrochloric acid and extracted with diethyl ether. The extract is washed with water, dried over magnesium sulphate and evaporated. This gives 24.3 g (100% of theory) of a pale yellow residue (melting point 80°–81° C.), which consists exclusively of cis- and trans-2-(2',2',2'-trichloroethyl)-3,3-dimethylcyclopropanecarboxylic acid. The mixture can be separated into the pure cis and trans compounds by fractional crystallization or by column chromatography.

NMR spectrum (100 MHz, CDCl$_3$/D$_2$O) in ppm: 2.75–3.33 (m, 2H); 1.50–1.97 (m, 2H); 1.32 (s, 2×CH$_3$ cis); 1.27 and 1.38 (2×s, 2×CH$_3$ trans).

(b) 8.0 g (30.3 mmols) of 2-(2',2',2'-trichloroethyl)-3,3-dimethyl-4-chlorocyclobutanone in 400 ml of acetone and 100 ml of water are irradiated, through pyrex glass, with a Philipps HPK 125 watt lamp until no further starting material can be detected by chromatography. The reaction mixture is evaporated and the residue is worked up to the acid as indicated under (a). This gives 6.95 g (93% of theory) of a cis/trans mixture of 2-(2',2',2'-trichloroethyl)-3,3-dimethylcyclopropanecarboxylic acid, the spectroscopic data of which are identical to those of the mixture obtained according to (a).

(c) 24.55 g (0.1 mol) of 2-(2',2',2'-trichloroethyl)-3,3-dimethylcyclopropanecarboxylic acid are suspended in 350 ml of 10% strength sodium hydroxide solution and the suspension is stirred for 4.5 hours at a bath temperature of 100° C. The reaction solution is washed with diethyl ether, acidified with hydrochloric acid and extracted with chloroform. The extract is washed with water, dried over magnesium sulphate and evaporated. After crystallization from n-hexane, 17.55 g (84% of theory) of colorless 2-(2',2'-dichlorovinyl)-3,3-dimethylcyclopropanecarboxylic acid are obtained.

EXAMPLE 6

145 g (0.5 mol) of 2-bromo-4,4,4-trichlorobutyric acid chloride, 280 g (5 mols) of isobutylene and 600 ml of cyclohexane are initially introduced into an autoclave. 51 g (0.5 mol) of triethylamine in 500 ml of cyclohexane are pumped in at 65° C. in the course of 4 hours. The mixture is then stirred for a further 3 hours at this temperature. The reaction mixture is filtered. The filtrate is evaporated and the residue is crystallized from n-hexane. This gives 74.5 g (48% of theory) of 2-bromo-2-(2',2',2'-trichloroethyl)-3,3-dimethylcyclobutanone in the form of a light beige powder; melting point 46°–49° C.

IR spectrum (CHCl$_3$) in cm$^{-1}$: 1885 (CO).

$^1$H NMR spectrum (100 MHz, pyridine-d$_5$) in ppm: 3.79 (AB, 2H, CH$_2$); 3.10 (AB, 2H, CH$_2$); 1.37 and 1.42 (1s in each case, total 6H, CH$_3$ in each case).

$^{13}$C NMR spectrum (CDCl$_3$) in ppm: 196.8 (CO); 95.6 (CCl$_3$); 74.8 (C-2); 56.5 and 56.3 (CH$_2$ in each case); 38.0 (C-3); 27.4 and 24.7 (CH$_3$ in each case).

20 g (0.065 mol) of 2-bromo-2-(2',2',2'-trichloroethyl)-3,3-dimethylcyclobutanone and 5 g of tetrabutylammonium bromide are stirred for 30 minutes at 80° C. and for 10 minutes at 100° C. The solidified melt is chromatographed on silica gel (elution with toluene/cyclohexane, 1:1). 2-(2',2',2'-Trichloroethyl)-3,3-dimethyl-4-bromocyclobutanone, which crystallizes on standing, is obtained in this way: melting point 56° C.

$^1$H NMR spectrum (100 MHz, CDCl$_3$) in ppm: 4.99 (d, J=2 Hz, 1H, H on C-4); 3.58 (X moiety of ABX, additionally resolved with J=2 Hz, 1H, H on C-2); 3.05 (AB moiety of ABX, 2H, CH$_2$); 1.22 and 2.67 (1s in each case, 3H in each case, CH$_3$ in each case).

$^{13}$C NMR spectrum (CDCl$_3$) in ppm: 196.7 (s, CO); 97.7 (s, CCl$_3$); 60.7 (d, C-2); 59.8 (d, C-4); 50.0 (t, CH$_2$-CCl$_3$); 36.4 (s, C-3); 27.6 (q, CH$_3$); 21.0 (q, CH$_3$).

A solution of 3.2 g of NaOH in 70 ml of water is added to 3.1 g (10.6 mmols) of 2-(2',2',2'-trichloroethyl)-3,3-dimethyl-4-bromocyclobutanone and the mixture is stirred for 2 hours. It is then stirred for a further 3 hours at 100° C. The reaction mixture is washed with diethyl ether and acidified with dilute hydrochloric acid. This aqueous phase is extracted with diethyl ether. The extract is washed with water, dried over magnesium sulphate and evaporated. The residue is crystallized from n-hexane. This gives 2.55 g of cis-2-(2',2'-dichlorovinyl)-3,3-dimethylcyclopropanecarboxylic acid; melting point 86° C.

IR spectrum (CHCl$_3$) in cm$^{-1}$: 1710 (CO), 1625 (C=C).

NMR spectrum (100 MHz, CDCl$_3$/D$_2$O) in ppm: 1.30 (s, 6H, 2×CH$_3$); 1.85 (d, J=8.5 Hz, 1H, HC-1); 2.02–2.19 (m, 1H, HC-2); 6.17 (d, J=8 Hz, 1H, CH=CCl$_2$).

EXAMPLE 7

90.5 g (1 mol) of acrylic acid chloride, 364.8 g (1.1 mol) of carbon tetrabromide, 200 ml of acetonitrile and 5.0 g of copper-I chloride are heated at 115° C. for 6 hours. After cooling, the reaction mixture is distilled direct. This gives 136.6 g (33% of theory) of 2,4,4,4-tetrabromobutyric acid chloride; boiling point 135°–140° C., 12 mm Hg.

350 ml of cyclohexane are saturated with isobutylene at room temperature (20°–25° C.). 42.2 g (0.1 mol) of 2,4,4,4-tetrabromobutyric acid chloride are dissolved therein. 10.1 g (0.1 mol) of triethylamine in 50 ml of cyclohexane are then added dropwise at room temperature in the course of 2 hours, with stirring and under a gentle stream of isobutylene. The resulting reaction mixture is stirred for 3 hours and water is then added. The organic layer is separated off, washed with water, dried over magnesium sulphate and evaporated. The residue is filtered through silica gel (eluant: cyclohexane/toluene, 1:1 mixture by volume). The filtrate is evaporated. The residue is crystallized from n-hexane.

2-Bromo-2-(2',2',2'-tribromoethyl)-3,3-dimethylcyclobutanone is obtained; melting point 61°–63° C.

IR Spectrum (CHCl$_3$) in cm$^{-1}$: 1780 (CO).

$^1$H NMR spectrum (100 MHz, CDCl$_3$) in ppm: 3.97 (AB, 2H, CH$_2$); 3.13 (AB, 2H, CH$_2$); 1.51 and 1.61 (1s in each case, 3H in each case, CH$_3$ in each case).

$^{13}$C NMR spectrum (CDCl$_3$) in ppm: 196.7 (CO); 76.8 (C-2); 60.0 and 56.6 (CH$_2$ in each case); 38.1 (C-3); 31.7 (CBr$_3$); 27.7 and 25.0 (CH$_3$ in each case).

9.6 g (21.8 mmols) of 2-bromo-2-(2',2',2'-tribromoethyl)-3,3-dimethylcyclobutanone and 2.0 g of tetrabutylammonium bromide are stirred at 90° C. for 30 minutes. The cooled melt is chromatographed on silica gel (elution with toluene/cyclohexane, 1:1). This gives 2-(2',2',2'-tribromoethyl)-3,3-dimethyl-4-bromocyclobutanone in the form of an oil which crystallizes slowly and which is recrystallized from diethyl ether/n-hexane; melting point 91°–93° C.

IR spectrum (CHCl$_3$) in cm$^{-1}$: 1795 (CO).

$^1$H NMR spectrum (100 MHz, CDCl$_3$) in ppm: 4.96 (d, J=2 Hz, 1H, H on C-4); 3.12–3.67 (ABX, the X moiety additionally being resolved with J=2 Hz, 3H, CH$_2$—CH); 1.18 and 1.67 (1s in each case, 3H in each case, CH$_3$ in each case).

$^{13}$C NMR spectrum (CDCl$_3$): 196.4 (s, CO); 63.2 (d, C-2); 59.9 (d, C-4); 54.6 (t, CH$_2$); 38.4 (s, CBr$_3$); 36.4 (s, C-3); 27.8 and 21.3 (q in each case, CH$_3$ in each case).

700 mg (1.56 mmols) of 2-(2',2',2'-tribromoethyl)-3,3-dimethyl-4-bromocyclobutanone are stirred with a solution of 190 mg of NaOH in 5 ml of water, to which 0.5 ml of dioxane has been added, for 2 hours at room temperature. The mixture is then stirred for 1 hour at 80° C. The clear solution is worked up to the acid in the customary way. 410 mg (88% of theory) of cis-2-(2',2'-dibromovinyl)-3,3-dimethylcyclopropanecarboxylic acid are obtained.

IR spectrum (CHCl$_3$) in cm$^{-1}$: 1695 (CO).

NMR spectrum (100 MHz, CDCl$_3$/D$_2$O) in ppm: 6.70 (6d, J=8 Hz, 1H, CH-CBr$_2$); 1.82–2.14 (m, 2H); 1.30 and 1.33 (1s in each case, total 6H, CH$_3$ in each case).

EXAMPLE 8

10.1 g (0.1 mol) of triethylamine in 100 ml of cyclohexane are added dropwise in the course of 2 hours, at 65° C., to a solution of 14 g (0.17 mol) of methylenecyclopentane and 26.4 g (0.1 mol) of 2,4,4,4-tetrachlorobutyric acid chloride in 220 ml of cyclohexane, with stirring. The mixture is then stirred at this temperature for a further 3 hours. The reaction mixture is washed with dilute hydrochloric acid and then with water, dried over magnesium sulphate and evaporated. The residue is crystallized from n-hexane. This gives 16.6 g of 1-chloro-1-(2',2',2'-trichloroethyl)spiro[3.4]octan-2-one of the formula

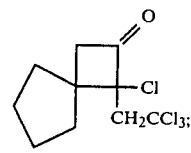

melting point 70°–73° C.

IR spectrum (CHCl$_3$) in cm$^{-1}$: 1775 (CO).

NMR spectrum (100 MHz, CDCl$_3$) in ppm: 1.60–2.30 (m, 8H); 3.08 (AB, 2H, CH$_2$); 3.60 (AB, 2H, CH$_2$).

12.0 g (0.041 mol) of 1-chloro-1-(2',2',2'-trichloroethyl)spiro[3.4]octan-2-one are stirred with 3.6 g of tetrabutylammonium chloride at a bath temperature of 125° C. After 1.5 hours, the reaction mixture is chromatographed on silica gel (elution with toluene/cyclohexane, 1:1). 9.7 g (81% of theory) of 1-chloro-3-(2',2',2'-trichloroethyl)spiro[3.4]octan-2-one of the formula

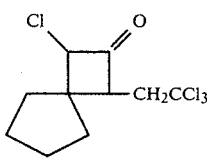

are obtained in this way in the form of a colorless oil.

IR spectrum (CHCl$_3$) in cm$^{-1}$: 1800 (CO).

NMR spectrum (100 MHz, CDCl$_3$) in ppm: 4.87 (d, J=2 Hz, 1H, CHCl); 3.70 (X moiety of ABX, additionally resolved with J=2 Hz, 1H, CH): 2.73–3.29 (AB moiety of ABX, 2H, CH$_2$); 1.45–2.23 (m, 8H).

4.83 g (16.6 mmols) of 1-chloro-3-(2',2',2'-trichloroethyl)spiro[3.4]octan-2-one are added to a solution of 2.0 g of NaOH in 40 ml of water and 3 ml of dioxane and the mixture is stirred for 2 hours at room temperature and then for 3 hours at 100° C. The reaction solution is washed with diethyl ether and acidified with dilute hydrochloric acid. The acid solution is extracted with diethyl ether. The extracts are washed with water, dried over magnesium sulphate and evaporated. The residue is crystallized from n-hexane. This gives 3.3 g of 2-(2',2'-dichlorovinyl)spiro[2.4]heptane-1-carboxylic acid of the formula

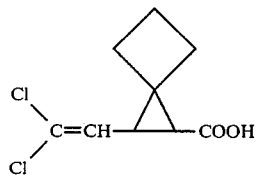

in the form of a white powder; melting point 90°–105° C.

IR spectrum (CHCl$_3$) in cm$^{-1}$: 1705 (CO), 1620 (C=C).

NMR spectrum (100 MHz, CDCl$_3$/D$_2$O) in ppm: 6.15 (d, J=9 Hz, 0.8H, CH=CCl$_3$cis); 5.51 (d, J=9 Hz, 0.2H, CH=CCl$_2$ trans); 2.00–2.40 (m, 2H); 1.60–1.95 (m, 8H).

EXAMPLE 9

33.6 g (0.62 mol) of methylenecyclopropane and 152 g (0.62 mol) of 2,4,4,4-tetrachlorobutyric acid chloride in 620 ml of n-pentane are initially introduced into a 2.5 liter autoclave. 62.8 g (0.62 mol) of triethylamine in 120 ml of n-pentane are pumped in in the course of 6 hours, at 60° C., and the reaction mixture is then kept at 60° C. for 6 hours. The reaction mixture is filtered, the filtrate is evaporated and the residue is distilled in vacuo. The fraction having a boiling range of 45°–80° C./0.09 mm Hg is then chromatographed on 250 g of silica gel using hexane/0–50% by weight toluene. The pure fractions are evaporated and the residue is distilled. This gives 1-chloro-1-(2',2',2'-trichloroethyl)spiro[3.2]hexan-2-one of the formula

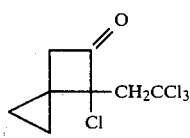

having a boiling point of 70°–71° C./0.08 mm Hg.

IR spectrum (CHCl$_3$) in cm$^{-1}$: 1776 (CO).

$^1$H NMR spectrum (100 MHz CDCl$_3$) in ppm: 0.8–1.8 (m, 4H); 2.6–3.8 (m, 4H).

A solution of 11.0 g (42 mmols) of 1-chloro-1-(2',2',2'-trichloroethyl)spiro[3.2]hexan-2-one and 1.17 g (6.3 mmols) of tributylamine in 15 ml of toluene is refluxed for 5 hours. After cooling, the reaction mixture is diluted with n-pentane. The mixture is washed with 2 N sulphuric acid and then with saturated sodium chloride solution, dried over sodium sulphate and evaporated. The residue is distilled in vacuo. This gives 1-chloro-3-(2',2',2'-trichloroethyl)spiro[3.2]hexan-2-one of the formula

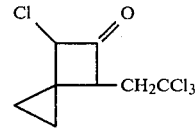

having a boiling point of 60° C./0.01 mm Hg.

IR spectrum (CCl$_4$) in cm$^{-1}$: 1780 (CO).

NMR spectrum (100 MHz, CDCl$_3$) in ppm: 0.8–1.7 (m, 4H); 2.6–4.2 (m, 3H); 4.75, 5.15 (one d in each case; together 1H).

7.1 g (27 mmols) of 1-chloro-3-(2',2',2'-trichloroethyl)spiro[3.2]hexan-2-one, together with 54 ml (about 135 mmols) of 10% strength NaOH, are refluxed for 2 hours. After cooling, the mixture is washed with several portions of diethyl ether, acidified with sulphuric acid and extracted with diethyl ether. The ether extracts are evaporated after drying over sodium sulphate. A small amount of strongly polar impurities is removed by filtering on silica gel (eluant: diethyl ether). After concentrating the filtrate, 2-(2',2'-dichlorovinyl)spiro[2.2]pentane-1-carboxylic acid of the formula

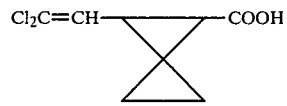

is obtained as an approximately 3:1 cis/trans mixture; melting point 77°–78° C.

IR spectrum (CCl$_4$) in cm$^{-1}$: 1675 (CO).

NMR spectrum (100 MHz, CDCl$_3$) in ppm: 0.8–2.85 (m, 6H); 5.56 and 6.11 (one d in each case, together 1H); 10.8 (broad s, 1H).

The examples which follow describe the preparation of some insecticidal active compounds.

EXAMPLE 10

Preparation of the m-phenoxybenzyl ester of 2-(2',2'-dichlorovinyl)-3,3-dimethylcyclopropane-1-carboxylic acid (a) 4.18 g (0.02 mol) of 2-(2',2'-dichlorovinyl)-3,3-dimethylcyclopropane-1-carboxylic acid and 20 ml of thionyl chloride are warmed at 70° C. for 3 hours. The excess thionyl chloride is then evaporated off, the residue is taken up in 100 ml of benzene and the mixture is evaporated again. A solution of 4.0 g (0.02 mol) of m-phenoxybenzyl alcohol in 40 ml of absolute benzene is added to this residue [2-(2',2'-dichlorovinyl)-3,3-dimethylcyclopropanecarboxylic acid chloride] and the mixture is warmed to 40° C. 2.2 g (0.022 mol) of triethylamine in 10 ml of absolute benzene are added dropwise to this mixture in the course of one hour and the reaction mixture is stirred for a further 1 hour at this temperature. The reaction mixture is washed with dilute hydrochloric acid, dried over magnesium sulphate and evaporated. The residue is chromatographed on silica gel using diethyl ether/n-hexane as the eluant (1:4 mixture by volume). This gives the m-phenoxybenzyl ester of 2-(2',2'-dichlorovinyl)-3,3-dimethylcyclopropane-1-carboxylic acid having a refraction of $n_D^{20} = 1.5628$.

(b) 5.28 g (0.02 mol) of 2-(2',2',2'-trichloroethyl)-3,3-dimethyl-4-chlorocyclobutan-1-one, dissolved in 25 ml of absolute dimethoxyethane, are added dropwise to a solution of 4.0 g (0.02 mol) of m-phenoxybenzyl alcohol, 0.5 g (0.021 mol) of NaH and 40 ml of absolute dimethoxyethane. The reaction mixture is then stirred for 1 hour at 45° C., 2.25 g (0.02 mol) of potassium tert.-butylate are then added and the mixture is refluxed for 3 hours. After it has been discharged into water, it is acidified with dilute hydrochloric acid and extracted with benzene. The evaporated extract is chromatographed on silica gel using diethyl ether/n-hexane as the eluant (1:4 mixture by volume). This gives the m-phenoxybenzyl ester of 2-(2',2'-dichlorovinyl)-3,3-dimethylcyclopropane-1-carboxylic acid in the form of a viscous oil, which has the same properties as the substance obtained according to (a).

EXAMPLE 11

β-Cyano-m-phenoxybenzyl cis-2-(2',2'-dichlorovinyl)-3,3-dimethylcyclopropanecarboxylate (1) 10 g (0.047 mol) of cis-2-(2',2'-dichlorovinyl)-3,3-dimethylcyclopropanecarboxylic acid in 100 ml of benzene are stirred with 12.1 ml (0.141 mol) of oxalyl chloride for 24 hours at room temperature. After evaporating the reaction solution, the brown residue is distilled under reduced pressure. This gives 9.1 g of a clear liquid; boiling point 50° C./0.04 mm Hg. 3.0 g of this clear liquid are dissolved in 30 ml of toluene and 2 ml of pyridine are added. 2.9 g of α-cyano-m-phenoxybenzyl alcohol in 20 ml of toluene are added dropwise to this mixture at room temperature and the reaction mixture is then stirred for a further 16 hours at room temperature. The reaction mixture is washed, first with water, then with saturated sodium bicarbonate solution and subsequently with salt water, dried over magnesium sulphate and evaporated. The residue is chromatographed on silica gel (elution with diethyl ether/n-hexane, 1:2). This gives pure α-cyano-m-phenoxybenzyl cis-2-(2',2'-dichlorovinyl)-3,3-dimethylcyclopropanecarboxylate as a mixture of diastereomers. NMR spectrum (60 MHz, CDCl$_3$) in ppm; 1.20–1.43 (m, 6H, CH$_3$); 1.67–2.35 (m, 2H, 2×CH); 6.25 (d, J = 9 Hz, 1H, CH-CCl$_2$), 6.40 and 6.45 (1s in each case, 0.5H in each case, CH-CN); 6.98–7.65 (m, 9H).

EXAMPLE 12

7.8 g (0.1 mol) of absolute pyridine are added dropwise, at room temperature, to a solution of 22.75 g (0.1 mol) of crude 2-(2',2'-dichlorovinyl)-3,3-dimethylcyclopropanecarboxylic acid chloride [prepared according to Example 1a] and 21.5 g (0.1 mol) of 3-phenoxy-α-hydroxyethylbenzene in 250 ml of absolute toluene. The reaction mixture is stirred for 15 hours at room temperature (20°–25° C.), washed with dilute hydrochloric acid and then with water, dried (over sodium sulphate) and evaporated. The residue is chromatographed on silica gel using n-hexane/diethyl ether as the eluant (1:1 mixture by volume). This gives α-methyl-m-phenoxybenzyl 2-(2',2'-dichlorovinyl)-3,3-dimethylcyclopropanecarboxylate in the form of a colorless oil of $n_D^{20} = 1.563$.

EXAMPLE 13

(a) Preparation of 4,4,4-tribromobutyric acid chloride 324,8 g (1 mole) of 4,4,4-tribromobutyric acid is added to 600 g of thionylchloride and 1 ml of dimethylformamide and the whole is heated at first for 2 hours at 40° C. and subsequently for 3 hours at 75° C. Then the excess of thionyl chloride is evaporated and the residue is distilled in vacuo. 360 g (95% of theory) of 4,4,4-tribromobutyric acid chloride, b.p. 71°–73° C./0,05 torr, is obtained.

(b) Preparation of 2-chloro-4,4,4-tribromobutyric acid chloride

To a solution of 343,2 g (1 mole) 4,4,4-tribromobutyric acid chloride in 600 g of thionylchloride 266,0 g (2 mole) of N-chlorosuccinimide is added portion wise at 60° C. while the reaction mixture is irradiated with a mercury high-pressure lamp. After addition of the N-chlorosuccinimide the reaction mixture is stirred for 5 hours at 60° C. while irradiation is continued. Then the thionyl chloride is evaporated and the residue is distilled in vacuo. 309.7 (82% of theory) of 2-chloro-4,4,4-tribromobutyric acid chloride, b.p. 59°–63° C./0,05 torr is obtained.

(c) Preparation of 2-(2',2',2'-tribromoäthyl)-2-chloro-3,3-dimethylcyclobutan-1-one 90,6 g (0, 24 mole) of 2-chloro-4,4,4-tribromo-butyric and chloride and 360 ml of cyclohexane are placed in an autoclave and 134 g (2,4 mole) of isobutylene is introduce under pressure. Then a solution of 24,2 g (0,24 mole) of triethylamine in 120 ml of cyclohexane is added at 65° C. during 4 hours and, after addition of the triethylamine, the temperature is kept at 65° C. for additional 3 hours. Thereafter the triethylamine hydrochloride formed is filtered off and the solvent is evaporated. The residue is dissolved in a solvent mixture consisting of equal parts of toluene and hexane and the solution is filtered over silica gel. After evaporation of the solvent from the filtrate 51,4 g (54% of theory) of 2-(2',2',2'-tribromoethyl)-2-chlor-3,3-dimethylcyclobutan-1-one, melting point 95°–97° C., is obtained.

IR spectrum (CCl$_4$) in cm$^{-1}$: 1800 (CO).

$^1$H-NMR spectrum (100 MHz, CDCL$_3$) in ppm: 1.39 and 1.41 (s. 3H); 2,86–3,22 (m, 2H); 3,55–4,15 (m, 2H).

(d) Preparation of 2-(2',2',2'-tribromoethyl)-3,3-dimethyl-4-chlorocyclobutan-1-one 22,8 g (0,054 mole) of 2-(2',2',2'-tribromoethyl)-2-chloro-3,3-dimethylcyclobutan-1-on is dissolved in 220 ml of absolute ethanol saturated with hydrogen chloride and the solution is stirred for 5 hours at 80° C. Then solvent is evaporated until the volume of the reaction mixture is reduced to one third of the starting volume and, after addition of water, the mixture is extracted with ether. The etheral extract is washed at first with saturated sodium chloride solution and subsequently with sodium bicarbonate solution and thereafter dried over sodium sulphate. The residue obtained after evaporation of the ether is purified by chromatography on silica gel using toluene as eluent. After combination of the pure fractions and evaporation of the solvent there is obtained 17,1 g (75% of theory) of 2-(2',2',2'-tribromoethyl)-3,3-dimethyl-4-chloro-cyclobutane-1-one, melting point 87°–89° C.

IR spectrum (CCl₄) in cm⁻¹: 1805 (CO). ¹H-NMR spectrum (100 MHz, CDCl₃) in ppm: 1,14 and 1,67 (s, 3H); 3,08–3,68 (m, 3H); 4,77 (d, 1H).

(2) Preparation of 2-(2',2',-dibromovinyl)-3,3-dimethylcyclopropane-1-carboxylic acid A mixture of 800 mg (0,02 mole) of 2-(2',2',2'-tribromoethyl)-3,3-dimethyl-4-chlorocyclobutan-1-one and 5,6 ml of 5% by weight of aqueous sodium hydroxide solution is stirred for 18 hours at 0° C. and subsequently for one additional hour at 80° C. Then the reaction mixture is cooled to room temperature washed with diethyl ether, acidified with concentrated hydrochloric acid and extracted with diethyl ether. The extract is washed with water and dried over magnesium sulphate. After evaporation of the diethyl ether there is obtained 0,59 g (100% of theoriy) of 2-(2',2'-dibromovinyl)-3,3-dimethylcyclopropane-1-carboxylic acid consisting to 80% of the cis-isomer and to 20% of the trans-isomer.

IR spectrum (CHCl₃) in cm⁻¹: 1695 (CO).

¹H-NMR spectrum (100 MHz, CDCl₃) in ppm: 1,25 (s, CH₃ group of trans-isomer), 1,35 (s, CH₃ group of trans-isomer), 1,30 (s, CH₃ group of cis-isomer); 1,31 (s, CH₃ group of cis-isomer); 1.62–2,30 (m, 2H); 6,15 and 6,70 (d, ratio of intensity 1:4, integral=1H).

What is claimed is:

1. A process for the preparation of a 2-(2'-2'-2'-trihalogenoethyl)-4-halogenocyclobutan-1-one of the formula I

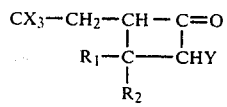

in which one of the radicals R₁ and R₂ is methyl and the other is hydrogen or methyl, R₁ and R₂ together are an alkylene group having 2 to 4 carbon atoms, and X and Y are each chlorine or bromine, which comprises reacting, at a temperature of from about 0°–200° C., a 2,4,4,4-tetrahalogenobutyric acid chloride of the formula II

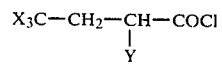

in which X and Y are as defined under formula I, in the presence of an organic base with an olefin of the formula III

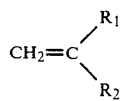

in which R₁ and R₂ are as defined under formula I, said base and said olefin being, respectively, present in at least equimolar amounts relative to said acid chloride, to give a 2-(2',2',2-trihalogenoethyl)-2-halogenocyclobutan-1-one of the formula IV

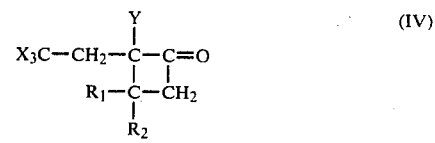

in which R₁, R₂, X and Y are defined under formula I, and then rearranging the latter, in the presence of about 0.1 to 15%, by weight of said butane-1-one, of an acid, base or quaternary ammonium halide catalyst, into a 2-(2',2',2'-trihalogenoethyl)-4-halogenocyclobutan-1-one of the formula I; said rearrangement being conducted at a temperature of from about 60°–150° C. when in a melt system and at a temperature of 0°–150° C. when in an inert organic solvent system.

2. A process according to claim 1, which comprises using 2,4,4,4-tetrachlorobutyric acid chloride as the 2,4,4,4-tetrahalogenobutyric acid chloride of the formula II.

3. A process according to claim 1, which comprises using 2-chlor-4,4,4-tribromobutyric acid chloride of the formula II.

4. A process according to claim 1, which comprises using an olefin of the formula III in which one of the radicals R₁ and R₂ is methyl and the other is hydrogen or methyl, or R₁ and R₂ together are an alkylene group having 2 to 3 carbon atoms.

5. A process according to claim 1, which comprises using isobutylene as the olefin of the formula III.

6. A process according to claim 1, which comprises using methylenecyclopropane as the olefin of the formula III.

7. A process according to claim 1, which comprises carrying out the reaction of a 2,4,4,4-tetrahalogenobutyric acid chloride of the formula II with an olefin of the formula III in the presence of pyridine or of a trialkylamine having 1 to 4 carbon atoms in each alkyl group and in the presence of an inert organic solvent.

8. A process according to claim 1, which comprises carrying out the reaction of a 2,4,4,4-tetrahalogenobutyric acid chloride of the formula II with an olefin of the formula III in the presence of triethylamine.

9. A process according to claim 1, which comprises using an inorganic or organic proton acid as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

10. A process according to claim 1, which comprises using a hydrogen halide acid as the catalyst for the rearrangement of a 2-(2',2',2'-trihalogenoethyl)-2-halogenocyclobutan-1-one of the formula IV into a 2-(2',2',2'-trihalogenoethyl)-4- halogenocyclobutan-1one of the formula I.

11. A process according to claim 1, which comprises using an organic base as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

12. A process according to claim 1, which comprises using an amine of the formula

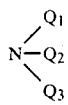

in which $Q_1$ is alkyl having 1 to 8 carbon atoms, cycloalkyl having 5 to 6 carbon atoms, benzyl or phenyl and $Q_2$ and $Q_3$ independently of one another are hydrogen or alkyl having 1 to 8 carbon atoms, as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

13. A process according to claim 1, which comprises using a salt of a proton acid with ammonia, a nitrogen-containing organic base or a quaternary ammonium salt as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

14. A process according to claim 1, which comprises using a salt of a hydrogen halide acid with an aliphatic, cycloaliphatic, araliphatic or aromatic primary, secondary or tertiary amine or a heterocyclic nitrogen base as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

15. A process according to claim 1, which comprises using a salt of the formula

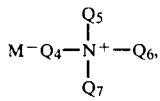

in which M is fluorine, bromine or iodine and especially chlorine, $Q_4$ is hydrogen, alkyl having 1 to 18 carbon atoms, cyclohexyl, benzyl, phenyl or naphthyl and $Q_5$, $Q_6$ and $Q_7$ independently of one another are hydrogen or alkyl having 1 to 18 carbon atoms, or a N-alkylpyridinium halide having 1 to 18 carbon atoms in the alkyl group, as the catalyst for the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I.

16. A process according to claim 1, which comprises carrying out the rearrangement of a 2-(2',2',2'-trihalogenoethyl)-2-halogenocyclobutan-1-one of the formula IV into a 2-(2',2',2'-trihalogenoethyl)-4-cyclobutan-1-one of the formula I at temperatures of between 80° and 130° C.

17. A process according to claim 1, which comprises carrying out the rearrangement of a 2-(2',2',2'-trihalogenoethyl)-2-halogenocyclobutan-1-one of the formula IV into a 2-(2',2',2'-trihalogenoethyl)-4-cyclobutan-1-one of the formula I in the melt at a temperature of between 80° and 130° C. in the presence of a trialkylamine having 1 to 8 carbon atoms in each alkyl group or of a tetraalkylammonium halide having 1 to 18 carbon atoms in the alkyl groups.

18. A process according to claim 1, which comprises carrying out the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I in the presence of an inert solvent.

19. A process according to claim 1, which comprises carrying out the rearrangement of a 2-(2',2',2'-trihalogenoethyl)-2-halogenocyclobutan-1-one of the formula IV into a 2-(2',2',2'-trihalogenoethyl)-4-halogenocyclobutan-1-one of the formula I in an aliphatic alcohol having 1 to 4 carbon atoms, toluene, xylene, chlorobenzene, dioxane, acetonitrile, 3-methoxypropionitrile, ethylene glycol, diethyl ether or diisopropyl ketone, as the solvent.

20. A 2-(2',2',2'-trihalogenoethyl)-2-halogenocyclobutan-1-one of the formula IV

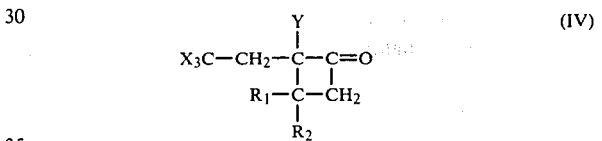

in which one of the radicals $R_1$ and $R_2$ is methyl and the other is hydrogen or methyl, or $R_1$ and $R_2$ together are alkylene having 2 to 4 carbon atoms, and X and Y are each chlorine or bromine.

21. A 2-(2',2',2'-trihalogenoethyl)-4-halogenocyclobutan-1-one of the formula I

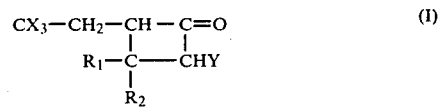

in which one of the radicals $R_1$ and $R_2$ is methyl and the other is hydrogen or methyl, or $R_1$ and $R_2$ together are alkylene having 2 to 4 carbon atoms, and X and Y are each chlorine or bromine.

* * * * *